US012082918B2

(12) United States Patent
Lesiv et al.

(10) Patent No.: US 12,082,918 B2
(45) Date of Patent: Sep. 10, 2024

(54) PREPARATION FOR MAGNETIC RESONANCE DIAGNOSTICS FOR ONCOLOGICAL DISEASES, COMPRISING DEUTERATED 2-AMINO-2-METHYLPROPIONIC ACID AND/OR 2-(N-METHYLAMINO)-2-METHYLPROPIONIC ACID, AND DIAGNOSTIC METHOD USING SAID PREPARATION

(71) Applicant: SOLVEX LIMITED LIABILITY COMPANY, Moscow (RU)

(72) Inventors: Aleksei Valerievich Lesiv, Dolgoprudny (RU); Pavel Evgenievich Ivashkin, Moscow (RU); Mikhail Vladimirovich Gulyaev, Moscow (RU); Evgeniya Olegovna Dorofeeva, Moscow (RU); Aleksei Viktorovich Kosenkov, Moscow (RU); Mikhail Valentinovich Kiselevsky, Moscow (RU); Vladimir Ivanovich Polshakov, Moscow (RU)

(73) Assignee: SOLVEX LIMITED LIABILITY COMPANY, Moscow (RU)

( * ) Notice: Subject to any disclaimer, the term of this patent is extended or adjusted under 35 U.S.C. 154(b) by 539 days.

(21) Appl. No.: 16/765,943

(22) PCT Filed: Nov. 21, 2017

(86) PCT No.: PCT/RU2017/000870
§ 371 (c)(1),
(2) Date: May 21, 2020

(87) PCT Pub. No.: WO2019/103636
PCT Pub. Date: May 31, 2019

(65) Prior Publication Data
US 2020/0352472 A1 Nov. 12, 2020

(51) Int. Cl.
A61B 5/055 (2006.01)
A61K 49/10 (2006.01)
C07C 229/08 (2006.01)

(52) U.S. Cl.
CPC .............. A61B 5/055 (2013.01); A61K 49/10 (2013.01); C07C 229/08 (2013.01)

(58) Field of Classification Search
CPC .................................. A61K 49/10; A61B 5/055
See application file for complete search history.

(56) References Cited

U.S. PATENT DOCUMENTS 4,371,611 A * 2/1983 Fusee ................... C12N 11/093
435/14
5,042,488 A 8/1991 Ackerman
6,574,496 B1 6/2003 Golman et al.
2003/0211036 A1 11/2003 Degani et al.
2007/0104648 A1* 5/2007 Shull ...................... A61K 49/10
424/9.3
2010/0322865 A1 12/2010 Duerk et al.
2011/0033382 A1* 2/2011 Goodman .............. A61B 6/481
424/1.89

FOREIGN PATENT DOCUMENTS

JP 2005-523941 8/2005
WO 2010/033511 A1 3/2010

OTHER PUBLICATIONS

Kresten Bertelsen et. al. Membrane-Bound Conformation of Peptaibols with Methyl-Deuterated r-Amino Isobutyric Acids by 2H Magic Angle Spinning Solid-State NMR Spectroscopy, JACS, 129, 14717-14723. (Year: 2007).*
Masakazutanaka et al. Helical structures of homo-chiral isotope-labeled alpha aminoisobutyric acid peptides, Tetrahedron, 72, 5864-5871. (Year: 2016).*
Sunwen Chou et al., "Oxidation and Mass Spectra of 4,4-Dimethyloxazolidine-N-oxyl (Doxyl) Derivatives of Ketones," J. Org. Chem., vol. 39, No. 16, Feb. 1974, pp. 2356-2361.
Kuninobu Kabuto et al., "A facile NMR method for assigning absolute configuration of underivatized [alpha]-methyl-[alpha]-amino acids using a chiral lanthanoid shift reagent for aqueous solution," Tetrahedron Letters, vol. 31, No. 7, 1990, pp. 1031-1034.
Tsuneomi Kawasaki et al., "Enantioselective Synthesis Included by Compounds with chirality arising from partially deuterated methyl groups in conjunction with asymmetric autocatalysis," Chemistry Letters, vol. 40, No. 3, Feb. 2011, pp. 320-321.
Robert A. Knight et al., "Quantitation and localization of blood-to-brain influx by magnetic resonance imaging and quantitative autoradiography in a model of transient focal ischemia," Magnetic Resonance in Medicine 54, Sep. 2005, pp. 813-821.

(Continued)

Primary Examiner — Michael G. Hartley
Assistant Examiner — Jagadishwar R Samala
(74) Attorney, Agent, or Firm — Nixon & Vanderhye PC

(57) ABSTRACT

The invention relates to medicine, particularly to agents for magnetic resonance diagnostics for oncological diseases. Developed for this purpose are a diagnostic preparation and a diagnostic method based on using said diagnostic preparation, in which a deuterated derivative of 2-amino-2-methylpropionic acid or 2-(N-methylamino)-2-methylpropionic acid and/or a pharmaceutically acceptable salt thereof, or a mixture of at least two deuterated derivatives of 2-amino-2-methylpropionic acid and/or 2-(N-methylamino)-2-methylpropionic acid and/or the pharmaceutically acceptable salt thereof is used as said preparation. The method according to the invention includes conducting magnetic resonance imaging and/or magnetic resonance spectroscopy on deuterium nuclei at a time after administration of the diagnostic preparation sufficient for the diagnostic preparation to accumulate in the tumor tissue of a subject in order to produce a magnetic resonance image and/or a magnetic resonance spectrum accordingly. The proposed method enables a highly informed diagnosis of oncological diseases.

17 Claims, 12 Drawing Sheets

(56) References Cited

OTHER PUBLICATIONS

Dieter Leibfritz et al., "NMR-Spectroscopic Assignment of the Aib-Methyl groups in α-helical and β-turn environment with the use of selectively deuterated Aib the solution conformations of Boc-Ala-Aib-Ala-OMe," Liebigs Ann. Chem 1989, Feb. 1989, pp. 1017-1027.

Jian Li et al., "Synthesis of deuterium-labeled hydroxybupropion," J. Label Compd. Radiopharm 2015, 58, Jul. 28, 2015, pp. 411-413.

Masamichi Tsuboi et al., "Infrared Spectrum of [alpha]-Aminoisobutyric Acid and the assignment of the vibrational frequencies," vol. 32, No. 10, Mar. 3, 1959, pp. 1044-1050.

Atsushi Ueda et al., "Helical structures of homo-chiral isotope-labeled [alpha]-aminoisobutyric acid peptides," Tetrahedron, vol. 72, Issue 39, Sep. 2016, pp. 5864-5871.

Sindhaghatta D. Venkataramu et al., "High resolution spin labeled fatty acid: synthesis and EPR spectral characteristics," Tetrahedron Letters, vol. 26. No. 11, pp. 1403-1406.

Sven Weigelt et al., "Synthesis of $^2$H-Labelled [alpha]-Azidoisobutyryl chloride(D6-azib-Cl) as 2H6-Aib equivalent building block in peptide synthesis," Letter, No. 4, pp. 726-728.

Thomas Weihrauch et al., "Darstellung „chiraler" α-Aminoisobuttersaure, Mar. 1985, pp. 1917-1921.

Peter S. Conti et al., "Tumor imaging with carbon-11 labeled alpha-aminoisobutyric acid (AIB) in a patient with advanced malignant melanoma," Eur J. Nucl Med. 1986, 12(7), pp. 353-356.

Kjell Någren et al., "[N-methyl-$^{11}$C]MeAIB, a tracer for system A amino acid transport: preparation from [$^{11}$C]methyl triflate and HPLC metabolite analysis of plasma samples after intravenous administration in man," Labelled Compounds and Radiopharmaceuticals, vol. 43, Issue 10, Sep. 2000, pp. 1013-1021.

* cited by examiner

A  B

A B

PREPARATION FOR MAGNETIC RESONANCE DIAGNOSTICS FOR ONCOLOGICAL DISEASES, COMPRISING DEUTERATED 2-AMINO-2-METHYLPROPIONIC ACID AND/OR 2-(N-METHYLAMINO)-2-METHYLPROPIONIC ACID, AND DIAGNOSTIC METHOD USING SAID PREPARATION

TECHNICAL FIELD

The invention relates to medicine, in particular to the means for magnetic resonance imaging in oncology.

BACKGROUND

Diagnostics for cancer, including early-stage detection, is a priority for the global health care. One of the powerful diagnostic methods for such diseases is the magnetic resonance imaging (MRI).

Most varieties of the MRI applied in the clinical practice, are based on the detection of proton magnetic resonance signal ($^1H$ nuclei), which are part of the water molecules in the human body. $^1H$ MRI provides a high degree of anatomical detail and in many cases allows to detect areas with abnormal signal corresponding to the tumors. At the same time, from the clinical practice it is known that the MRI is not always able to distinguish malignant tumors from benign ones, or those not requiring urgent treatment (low specificity of the method). In this context, early diagnosis of the oncological diseases is also hampered because of the high risk of a false positive result.

The main method of increasing the $^1H$ MRI diagnostic value is to use contrast agents that change the parameters of the signal in their vicinity [Topics in Current Chemistry, Contrast Agents I, Magnetic Resonance Imaging, Editors: Krause, Werner, 2002]. There is a wide range of contrast agents used in the MRI diagnostics, including commercially available Omniscan®, Magnevist®, ProHance®, and Clariscan®, which is a complex of gadolinium, as well as Feridex® and Resovist®, which are stable water suspensions of magnetic nanoparticles. These substances are injected into the bloodstream of the patient and assess the degree of blood supply to areas with suspected malignancy.

An alternative of performing $^1H$ MRI with contrast agents is a registration of the signal of the other nuclei, particularly $^{31}P$, $^{13}C$, $^{19}F$, $^2H$, $^{23}Na$. One of these nuclei is deuterium ($^2H$). This non-radioactive isotope of hydrogen, which natural content in biological objects is 0.0156%, and sensitivity is several times lower than that of the proton.

To date several cases of $^2H$ NMR and/or $^2H$ MRI application in vivo are described. The document US20030211036 A1 proposed a method of measuring the perfusion of the tumor tissues using isotope-labeled compounds, including deuterated compounds.

The document U.S. Pat. No. 5,042,488 demonstrated that it is possible to detect the background deuterium signal, as well as the signal resulting from the injection of $D_2O$ or 1-deuterated glucose in vivo (in a rat's liver). It is noted that the invention can also be implemented using other blood flow indicators labeled with deuterium.

The document US20100322865 A1 describes the use of metabolic precursors of water for estimating metabolic rate by carrying out the $^2H$-MRI. 1,2,3,4,5,6,6-deuterated glucose is given as an example of HOD metabolic precursor. Within the described invention only the deuterium NMR signals of the metabolic water and aliphatic chains of fatty acids are registered, but no NMR signals of the deuterated glucose.

None of the above methods is used in practice for the diagnostics of the oncological diseases, to a large extent due to the need of using very large doses of the deuterated compounds.

Despite the prominence of existing modalities of MRI, there is a need to develop new, more efficient approaches for the MRI diagnosis of the oncological diseases.

SUMMARY OF THE INVENTION

The object of the present invention is the development of new efficient diagnostic agent for diagnosis of the oncological diseases through MRI and/or MR spectroscopy, and a diagnostic method comprising the use of the specified agent.

The invention concerns the development of a new and efficient diagnostic agent that can be used in the diagnosis of oncological diseases, particularly breast cancer. Another technical result of the present invention is the development of the new efficient and informative diagnostic method for oncology by means of magnetic resonance imaging and/or magnetic resonance spectroscopy at the frequency of deuterium nuclei, that includes administration of the diagnostic agent according to the invention, said agent being able to accumulate in tumors in a sufficient concentration to register a deuterium MR image or a $^2H$-NMR spectrum in vivo.

The diagnostic agent according to the invention is characterized by the combination of such properties as: high content of deuterium atoms; its ability to accumulate in tumors within a reasonable time up to a concentration that is sufficient for the diagnostics; low toxicity and an almost complete excretion of the intact agent from the body. This allows for efficient diagnostics using dosages that are harmless to the human.

The method of the invention is not associated with any harmful effects of ionizing radiation (typical, for example, for the methods of CT, PET, SPECT), which in turn increases the safety of the studies and makes it possible to perform more frequent repeated studies, and makes the method suitable for pediatric patients. The invention is aimed at obtaining diagnostic information similar to that of the positron emission tomography (PET), but, unlike the latter, it allows to eliminate the risks associated with ionizing radiation of the radiopharmaceutical agents.

The present invention concerns the development of a diagnostic agent that includes a deuterated derivative of 2-amino-2-methylpropionic acid and/or 2-(N-methylamino)-2-methylpropionic acid and/or its pharmaceutically acceptable salt or a mixture of at least two different deuterated derivatives of 2-amino-2-methylpropionic acid and/or 2-(N-methylamino)-2-methylpropionic acid and/or its pharmaceutically acceptable salt, for the diagnosis of oncological diseases by magnetic resonance imaging and/or magnetic resonance spectroscopy at the frequency of deuterium nuclei.

In particular embodiments of the invention, the diagnostic agent additionally includes at least one additional pharmaceutically acceptable component. In particular embodiments of the invention pharmaceutically acceptable component is a carrier, filler and/or solvent.

In particular embodiments of the invention the deuterated derivative of 2-amino-2-methylpropionic acid is a 2-amino-2-($CD_3$)-3,3,3-$D_3$-propionic acid or 2-amino-2-($CD_2H$)-3,3,3-$D_3$-propionic acid or 2-amino-2-(CDH2)-3,3,3-D3-propionic acid or 2-amino-2-methyl-3,3,3-D3-propionic acid or 2-amino-2-(CD$_2$H)-3,3-D$_2$-propionic acid or 2-amino-2-(CDH$_2$)-3,3-D$_2$-propionic acid or 2-amino-2-methyl-3,3-D$_2$-propionic acid or 2-amino-2-(CDH2)-3-O-propionic acid or $_2$-amino-2-methyl-$_3$-D-propionic acid.

In particular embodiments of the invention the deuterated derivative of 2-(N-methylamino)-2-methylpropionic acid is 2-(N-methylamino)-2-(CD$_3$)-3,3,3-D$_3$-propionic acid or 2-(N-(CD$_3$)amino)-2-methylpropionic acid or 2-(N-(CD$_3$)amino)-2-(CD$_3$)-3,3,3-D$_3$-propionic acid.

In the other particular embodiments of the invention, the diagnostic agent is a mixture of at least two different deuterated derivatives of 2-amino-2-methylpropionic acid and/or 2-(N-methylamino)-2-methylpropionic acid selected from 2-amino-2-(CD$_3$)-3,3,3-D$_3$-propionic acid and/or 2-amino-2-(CD$_2$H)-3,3,3-D$_3$-propionic acid and/or 2-amino-2-(CD$_2$H)-3,3,3-D$_3$-propionic acid and/or 2-amino-2-methyl-3,3,3-D$_3$-propionic acid and/or 2-amino-2-(CD$_2$H)-3,3-D$_2$-propionic acid and/or 2-amino-2-(CDH$_2$)-3,3-D$_2$-propionic acid and/or 2-amino-2-methyl-3,3-D$_2$-propionic acid and/or 2-amino-2-(CDH$_2$)-3-D-propionic acid or 2-amino-2-methyl-3-D-propionic acid and/or 2-methylamino-2-(CD$_3$)-3,3,3-D$_3$-propionic acid and/or 2-(N-(CD$_3$)amino)-2-methylpropionic acid and/or 2-(N-(CD$_3$)amino)-2-(CD$_3$)-3,3,3-D$_3$-propionic acid.

In particular embodiments of the invention, the diagnostic agent of the invention optionally includes non-deuterated 2-amino-2-methylpropionic acid or 2-(N-methylamino)-2-methylpropionic acid.

In particular embodiments of the invention the deuterated derivative of 2-amino-2-methylpropionic acid or 2-(N-methylamino)-2-methylpropionic acid along with the deuterium atoms associated with carbon atoms, contain atoms of deuterium, partially or completely substituting mobile hydrogen atoms associated with oxygen atoms and/or nitrogen.

The invention also includes the process of obtaining the diagnostic agent according to the invention.

The present invention includes the implementation of the diagnostic method for oncological diseases, comprising the following stages:
  a) the diagnostic agent according to the invention is administered to the subject;
  b) the deuterium tomography and/or NMR spectrum, magnetic resonance imaging and/or magnetic resonance spectroscopy is carried out at the frequency of deuterium nuclei after a time sufficient for accumulation of the deuterated derivative of 2-amino-2-methylpropionic acid and/or 2-(N-methylamino)-2-methylpropionic acid and/or its pharmaceutically acceptable salt or mixtures of at least two different deuterated derivatives of 2-amino-2-methylpropionic acid and/or 2-(N-methylamino)-2-methylpropionic acid and/or its pharmaceutically acceptable salt in the tumor tissue, resulting in a $^2$H-MR image and/or a $^2$H-NMR spectrum, respectively;
  c) the presence or absence of an oncological disease is diagnosed based on the observed signal intensity of the deuterium nuclei, reflecting the level of accumulation of the deuterated derivative of 2-amino-2-methylpropionic acid and/or 2-(N-methylamino)-2-methylpropionic acid and/or a pharmaceutically acceptable salt thereof or mixtures of at least two different deuterated derivatives of 2-amino-2-methylpropionic acid and/or 2-(N-methylamino)-2-methylpropionic acid and/or a pharmaceutically acceptable salt thereof.

In particular embodiments of the invention, in the absence of accumulation areas of the diagnostic agent, a subject is diagnosed with absence of cancer.

In particular embodiments of the invention, at least one additional medical study is carried out, selected from the magnetic resonance imaging using nuclei differing from deuterium and/or ultrasound and/or computed tomography and/or x-ray and/or palpation and/or biopsy and/or analysis of biological fluids for tumor markers and/or radionuclide diagnostics and/or visual physical examination.

In particular embodiments of the invention the presence or absence of an oncological disease is diagnosed based on the comparison of signal intensity of deuterium nuclei with a typical intensity of the signal observed in healthy subjects in the corresponding tissue or organ.

In particular embodiments of the invention the presence or absence of an oncological disease is diagnosed based on the comparison of a signal intensity of the deuterium nuclei in the regions corresponding to normal and abnormal tissue according to additional medical studies.

In particular embodiments of the invention the presence or absence of an oncological disease is diagnosed based on a comparison of deuterium MR image with the image obtained through $^1$H-MRI.

In particular embodiments of the invention based on the observed signal intensity of the deuterium nuclei, the conclusion about the malignancy or aggressiveness or degree of differentiation of the tumor is made.

In particular embodiments of the invention, the diagnosed oncological disease is a breast cancer, glioma.

In particular embodiments of the invention, during the registration of a deuterium MR image the selective excitation of deuterium included in deuterated derivatives of 2-amino-2-methylpropionic acid and/or 2-(N-methylamino)-2-methylpropionic acid and/or its pharmaceutically acceptable salts, or mixtures deuterated derivatives of 2-amino-2-methylpropionic acid and/or 2-(N-methylamino)-2-methylpropionic acid and/or its pharmaceutically acceptable salt is used.

In particular embodiments of the invention, during the registration of a deuterium MR image the broadband excitation of the deuterium included in deuterated derivatives of 2-amino-2-methylpropionic acid and/or 2-(N-methylamino)-2-methylpropionic acid and/or its pharmaceutically acceptable salts, or mixtures deuterated derivatives of 2-amino-2-methylpropionic acid and/or 2-(N-methylamino)-2-methylpropionic acid and/or its pharmaceutically acceptable salt is used.

In particular embodiments of the invention, the diagnostic agent is administered to a subject orally.

In the other particular embodiments of the invention, the diagnostic agent is administered to a subject parenterally.

In particular embodiments of the invention the magnetic resonance imaging and/or magnetic resonance spectroscopy on the deuterium nuclei is carried out 20-360 minutes after the administration of the diagnostic agent.

In particular embodiments of the invention, the diagnostic agent is administered to a subject in an amount corresponding to 0.25-1 g of deuterated derivative of 2-amino-2-methylpropionic acid and/or 2-(N-methylamino)-2-methylpropionic acid and/or its pharmaceutically acceptable salts, or mixtures of deuterated derivatives of 2-amino-2-methylpropionic acid and/or 2-(N-methylamino)-2-methylpropionic acid and/or its pharmaceutically acceptable salt per 1 kg of body weight of a subject.

The invention also includes the use of the diagnostic agent according to the invention for diagnostics of an oncological disease by the magnetic resonance imaging and/or magnetic resonance spectroscopy at the deuterium frequency.

DEFINITIONS AND TERMS

Figure 1:
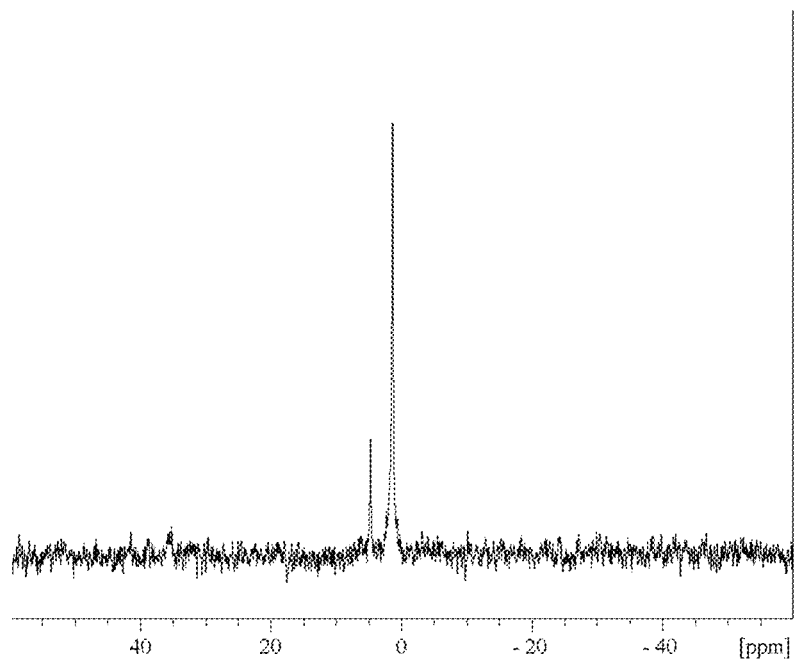
FIG. 1. $^2$H spectrum of the sample with 2-amino-2-(CD$_3$)-3,3,3-D$_3$-propionic acid FIG. 2. Deuterium MR image of the sample containing a dilute solution of deuterated diagnostic agent: (a) broadband excitation; (b) selective excitation at the frequency of 2-amino-2-(CD$_3$)-3,3,3-D$_3$-propionic acid.

For a better understanding of the present invention below are some terms used in this description of the invention.

In the description of this invention, the terms "includes" and "including" are interpreted as meaning "includes, among other things". These terms are not meant to be interpreted as "consists only of".

The term "deuterated derivative" in this document refers to a compound containing deuterium associated with carbon in excess of its natural content, at least in one position. In particular embodiments of the invention, the deuterium content, at least in one position, exceeds 30%, in other particular embodiments—90%. The "mixture of at least two different deuterated derivatives" refers to a mixture of compounds containing deuterium in different positions of the molecule, or containing different amounts of deuterium in the same position. The symbol "D" in this document denotes a hydrogen atom that is enriched with $^2$H isotope with respect to its natural content.

The term "voxel" in this document refers to a volume element in the sample that is freely selectable by adjusting the parameters of the magnetic field and produces the signal of the nuclear magnetic resonance.

As used herein, "pharmaceutically acceptable salt" term refers to those salts which are, according to the medical conclusion, suitable for being used in contact with the tissues of humans and animals without excessive toxicity, irritation, allergic reactions, etc., and demonstrate a reasonable ratio of risks and benefits. Pharmaceutically acceptable salts of amines, carboxylic acids, phosphonates and other types of compounds are well known in medicine. Salts can be prepared in situ during the process of isolation or purification of compounds of the invention and can be obtained separately by reacting the free acid or free base compounds of the invention with the appropriate base or acid, respectively. Examples of pharmaceutically acceptable, nontoxic salts of acids include salts of an amino group formed with inorganic acids such as hydrochloric, hydrobromic, phosphoric, sulfuric and perchloric acid, or organic acids such as acetic, oxalic, maleic, tartaric, succinic or malonic acid, or obtained by other methods used in this field, for example, using ion exchange. Other pharmaceutically acceptable salts include adipate, alginate, ascorbate, aspartate, benzenesulfonate, benzoate, bisulfate, borate, butyrate, camphorcarboxylate, camphorsulfonate, citrate, cyclopentanepropionic, digluconate, dodecyl sulfate, ethanesulfonate, formate, fumarate, glucoheptonate, glycerophosphate, gluconate, hemisulfate, heptanate, hexanate, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate and the like. Typical salts of alkali and alkaline earth metals include sodium, lithium, potassium, calcium, magnesium and others. In addition, pharmaceutically acceptable salts may contain, if required, non-toxic cations of ammonium, quaternary ammonium and amine, obtained using such counterions as halides, hydroxides, carboxylates, sulfates, phosphates, nitrates, lower alkanesulfonates and arenesulfonates.

The diagnostic agent according to the invention may comprise one or more pharmaceutically acceptable excipients that are suitable for specific forms of dosing, in particular, any carriers, solvents and/or excipients, which may be introduced into a patient's body together with the compound constituting the essence of this invention, and which do not negatively impact the deuterated compound, and are non-toxic when administered.

DETAILED DESCRIPTION OF THE INVENTION

For the successful implementation of a diagnostic method for oncological diseases using $^2$H MRI or $^2$H NMR one needs to achieve a sufficiently high deuterium concentration in the tumor tissue. To satisfy this criterion, a diagnostic agent:

1) should quickly and selectively accumulate in the tumor tissue (in particular, there should be a sufficiently efficient mechanism of membrane transport);
2) should be characterized with a rather slow excretion (which allows sufficient time for the accumulation of large quantities of the agent in the tumor, as well as for an extended registration of $^2$H MR images);
3) should not be significantly metabolized (minimizing possible side effects, including the incorporation of deuterium into the biomolecules, and allowing a repeated examination in as little as a few hours after the previous administration, without changing the background signal of the tumor);
4) should have low toxicity at the concentrations required (making it possible to administer sufficiently large doses of the agent);
5) should contain a large amount of deuterium (required to achieve sufficient signal intensity).

The authors of the present invention unexpectedly discovered that deuterated derivative of 2-amino-2-methylpropionic acid and/or 2-(N-methylamino)-2-methylpropionic acid according to the invention are capable of accumulating in tumor tissue in sufficient concentration to visualize tumors in vivo by $^2$H MRI method or $^2$H NMR, which in turn enables an efficient diagnosis of oncological diseases by the magnetic resonance imaging on the deuterium nuclei.

Due to the low content of deuterium in the body (0.015% of hydrogen atoms), background signals in the $^2$H MRI are several orders of magnitude lower than in $^1$H MRI. Thus, even at low concentrations of the diagnostic agent the signal is not superimposed with the natural background signal components. The development of similar methods using non-deuterated diagnostic agents on the basis of $^1$H MRI is complicated because of the presence of a large number of background signals of natural low molecular weight compounds with intensity comparable to the maximum achievable signal intensity of non-deuterated diagnostic agents. At the same time, the presence of the background HOD signal imposes restrictions on the minimum acceptable concentration for $^2$H MRI of a diagnostic agent in the tumor. The practical applicability of the diagnostic method according to the invention depends on the pharmacokinetics and pharmacodynamics of a particular diagnostic agent.

The ability to register the deuterium signal in vivo is also determined by presence of a sufficient number of deuterium atoms in the structure of the compound. So, the diagnostic agent according to the invention, comprising deuterated 2-amino-2-methylpropionic acid and/or 2-(N-methylamino)-2-methylpropionic acid containing one or more $CD_3$ groups is the preferred embodiment of the present invention. The presence of such deuterated groups allows to carry out MRI scans with the use of lower concentrations of the diagnostic agent, which minimizes side effects.

The method of the invention allows to diagnose the presence or absence of an oncological disease. The method according to the invention is based on the use of a deuterated diagnostic agent and the registration of MRI and/or NMR spectra at the frequency of deuterium.

It is known that $^1$H MRI by itself in many cases has insufficient diagnostic accuracy, whereas the method of the invention provides information about the molecular transportation of 2-amino-2-methylpropionic acid and/or 2-(N-methylamino)-2-methylpropionic acid, which are not available in traditional modes of $^1$H MRI, and thus potentially allows to obtain more accurate diagnostic information.

In one of the embodiments of the invention, the process of diagnostics involves MRI and is carried out as follows:

a) in some embodiments of the invention $^1$H MRI is carried out. Registration of $^1$H MRI allows, first, establish an anatomical reference frame for the deuterium signal, and secondly, to identify areas with suspected malignancy (in other embodiments of the invention, the definition of the field view of $^2$H MRI can be carried out in other ways, in particular by ultrasound, computed tomography, radiography, palpation, biopsy, analysis of biological fluids for tumor markers, radionuclide diagnostics, physical examination);

b) the diagnostic agent is administered;

c) after a time sufficient for accumulation of the diagnostic agent in the tumor tissue of a subject the $^2$H MR image is registered at the frequency of precession of the deuterium nuclei of the diagnostic agent;

d) obtained deuterium MR images are analyzed to find areas with anomalously high intensity and, therefore, responsible for the accumulation of the diagnostic agent. In particular, it is possible to compare the images obtained at $^1$H and $^2$H: if abnormal areas on $^1$H and $^2$H are matching, this means a higher probability of the present malignancy. However, the presence of abnormalities on $^1$H image is not a prerequisite: there may be situations when the tumor is not seen on the image obtained through $^1$H MRI, while the accumulation of the diagnostic agent is observed on the image obtained by $^2$H MRI. In the latter case, $^1$H MRI is used only for the anatomical referencing of a suspicious area.

In another particular embodiment of the invention, the process of diagnosis involves performing NMR spectroscopy at the frequency of deuterium and is carried out as follows:

a) $^1$H MRI is performed to identify regions with suspected malignancy (in other embodiments of the invention, the definition of the field of $^2$H NMR can be carried out in other ways, in particular by ultrasound, computed tomography, radiography, palpation, biopsy, analysis of biological fluids for tumor markers, radionuclide diagnostics, physical examination);

b) the diagnostic agent is administered;

c) after a time sufficient for accumulation of the diagnostic agent in the tumor tissue of a subject the spectrum of deuterium is registered (in particular, using local spectroscopy) in the voxels corresponding to the region of suspected malignancy (e.g., according to the results of $^1$H MRI; optionally the spectrum is registered in neighboring voxels or the signal intensity is compared; in particular embodiments the spectroscopy can be performed using a transmitting, transmitting-and-receiving, volume, implanted, or surface coils;

d) the signal intensity in voxels corresponding to the region of suspected malignancy is compared to: (i) typical values for this tissue (which shall be first defined in healthy subjects) and/or (ii) the intensity of the neighboring voxels corresponding to the same tissue or organ, and free of anomalies according to $^1$H MRI. Increased signal intensity suggests the accumulation of the diagnostic agent and, as a consequence the presence of a malignancy.

The order of the stages a), b), c) in both of the above specified embodiments of the invention may be different, for example, the diagnostic agent is administered, $^1$H MRI is carried out, then $^2$H MRI or NMR spectroscopy is performed; or $^1$H MRI is done after $^2$H MRI or $^2$H NMR spectroscopy.

In particular embodiments of the invention, after identifying the region with suspected malignancy individual voxels lying within and outside the suspicious region are selected (in particular, a series of the neighboring voxels lying on the same line crossing the border of a suspicious area can be selected). Registration of the integral signal of $^2$H or $^2$H spectra in the selected voxels with the following comparison of their intensity in the $^2$H channel allows to quickly and with greater sensitivity detect the accumulation of the diagnostic agent.

MR images and MR spectra according to the invention can be acquired using any MRI scanner equipped to register the signal of deuterium.

In particular embodiments of the invention, the use of the diagnostic agent, giving a signal in the region free of the background HOD signal, allows to carry out MRI with the use of selective excitation impulse configured on the frequency of the diagnostic agent. This eliminates the background signal of HOD on the image.

Through the use of molecular mechanisms of transportation and accumulation of the diagnostic agent according to the invention in cells, the method according to the invention enables the assessment of the metabolic activity of the tissue studied, and, consequently, to assess the malignancy or aggressiveness of the tumor. Thus, the diagnostic potential of the method is increased compared with the conventional $^1$H magnetic resonance imaging and the MRI methods based on the evaluation of perfusion (including typical contrast agents).

The signal of the diagnostic agent according to the invention may be registered up to 6 hours after the administration, and distribution of the agent in the tumor and other organs changes during this time. Thus, the signal of the diagnostic agent is primarily manifested in the liver and the kidneys, then in some areas of the tumor, probably corresponding to the areas of the most active growth and with the best blood supply. The maximum signal of deuterium in the whole volume of the tumor after intraperitoneal injection is observed in two hours, then the pattern of the distribution of the diagnostic agent keeps on changing. Because of such behavior, repeated imaging over several hours after the administration of the diagnostic agent according to the invention allows to obtain information both on the rate of membrane transportation, and the level of perfusion in different parts of the tumor, which in turn gives information about the structure and type of the tumor.

The experiments by the authors demonstrate the selectivity of accumulation of the agent according to the invention in tumor tissue compared to brain, skeletal muscles and other organs and tissues in acceptable to $^2$H MRI doses.

It is known that 2-amino-2-methylpropionic acid and 2-(N-methylamino)-2-methylpropionic acid are non-proteinogenic amino acids, thus their use does not lead to long-term fixation of deuterium in proteins. 2-Amino-2-methylpropionic acid and 2-(N-methylamino)-2-methylpropionic acid are not metabolized to form deuterated cofactors or other metabolites involved in basic biochemical processes. It is known from the prior art that the presence of deuterium can significantly alter the rates of enzymatic reactions, which in turn can lead to the accumulation of toxic intermediates and to other undesirable changes in metabolism. Thus, the lack of metabolism of the diagnostic agent according to the invention is a factor that reduces the likelihood of side effects. The conducted experiments showed the absence of metabolic transformations of the diagnostic agent according to the invention (the absence of new signals in $^2$H NMR spectrum of blood, urine, and also in vivo), regardless of the mode of administration. Thus, the observed dynamics of accumulation of the agent in the tumor and its subsequent elimination depends only on the rates of transportation between various tissues and blood and is not complicated by metabolic processes.

The research conducted by the authors demonstrated good tolerability of the diagnostic agent by animals, the absence of apparent side effects when used in indicated doses and complete removal of the deuterium-containing compounds from the body within a few hours. So, after intraperitoneal injection of the medications according to the invention to mice at a dosage of 8 g/kg the death of the animals was not observed, and in 72 hours after administration of the medication it was not observed in the tumor according to the $^2$H magnetic resonance imaging. The background concentration of deuterium in the tumor and other tissues remained the same, indicating that there is no long-term accumulation of the agent according to the invention in the body. Complete removal of deuterium from tumor tissue allows for repeated diagnostics after 72 hours and to monitor the dynamics of tumor development in the process of treatment.

The experiments showed that the results of the visualization of the tumor are significantly dependent on the dose of the diagnostic agent within the allowed range. Smaller doses allow to selectively visualize parts of the tumor with the most intense absorption, while increasing the dose leads to more complete filling of the boundaries of the tumor with the signal of deuterium. Because of this property of the diagnostic agent according to the invention it is possible to conduct dynamic studies (multiple registration of the images) with a gradual increase in the concentration of the agent in blood with time (e.g., slow intravenous infusion or series of successive injections of small doses of the agent). Such studies can provide information on metabolic activity of different parts of the tumor and on the extent of an oncological disease.

The method of the invention is carried out without the harmful effects of ionizing radiation (typical, for example, for the methods of CT, PET, SPECT), which in turn increases the safety of the studies, makes it possible to perform more frequent repeated studies, in particular, makes the method attractive for the pediatrics.

The diagnostic method according to the invention can be applied, in particular, for early diagnostics of tumors of different localization, metastatic lesions, evaluating tumor response to treatment and conclusions about the efficiency of the therapy, to confirm the diagnosis made on the basis of the $^1$H MRI results and/or other diagnostic methods.

The method according to the invention can be used for the diagnostics of various tumors, in particular breast tumor and glioma.

The method of the invention extends the existing methods of oncological diagnostics and enables an efficient diagnostic modality.

THE IMPLEMENTATION OF THE INVENTION

The possibility of objective manifestations of the technical result when using the invention is confirmed by reliable data given in the examples, containing experimental information obtained in the process of conducting research on methods adopted in this area. The invention is illustrated by the figures.

It should be understood that these and all examples given in the application materials are not limiting and are provided only to illustrate the present invention.

The examples given in this document illustrate the principle of the developed method, and do not limit the range of used doses and time interval between administration of the diagnostic agent and detection of deuterium, because, depending on the sensitivity and other parameters of the equipment used, diagnosed disease and the nature of a subject (human or laboratory animal) the required dose and time required for accumulation may differ. Furthermore, parameters of registration of the spectra and images, including the time of signal accumulation, are part of the specific embodiments of the invention and can vary depending on the equipment used and the specific diagnostic task.

Synthesis of 2-amino-2-($CD_3$)-3,3,3-$D_3$-propionic acid

The solution of 1.9 g of acetone-$d_6$ in 5 ml of diethyl ether is added at 0-5° C. to the solution of 2.0 g of ammonium chloride in 5 ml of $D_2O$. Then 1.6 g of sodium cyanide is slowly added in 3.5 ml of $D_2O$. The reaction mixture is stirred for one hour and left overnight. The ether layer is separated, the aqueous layer is extracted by six 3-ml portions of diethyl ether. The combined ether extracts are evaporated, the residue is dissolved in 8 ml of methanol. The resulting solution is saturated with gaseous ammonia and allowed to stand for 48 hours. The reaction mixture is evaporated, 6 ml of water and 10 ml of 48% hydrobromic acid are added to the residue, after which the mixture is boiled for 2 hours, then evaporated in vacuo and, after addition to the dry residue, 5 ml of water is evaporated again. The residue after evaporation is dissolved in 15 ml of methanol and filtered. 3 ml of pyridine is added to the obtained solution. In 10 hours, the crystalline 2-amino-2-($CD_3$)-3,3,3-$D_3$-propionic acid is filtered off, washed with methanol and dried in vacuum. Yield 1.1 g (35%)

$^1$H NMR ($D_2O$): 1.30 (residual signal of the protons of the methyl group).

$^{13}$C NMR ($D_2O$): 178.1, 23.5.

When $D_2O$ is used in hydrolysis, and also by keeping the final product in $D_2O$, followed by evaporation, deuterated 2-amino-2-($CD_3$)-3,3,3-$D_3$-propionic acid is obtained with partially or completely deuterated amino and carboxylic groups.

The possibility of detecting a deuterium MR image of a sample containing deuterated 2-amino-2-methylpropionic acid solution using a broadband and a selective radiofrequency pulse is shown (Example 1).

In vivo experiments (example 2-3) demonstrate the possibility of recording deuterium MR images and NMR spectra in vivo and the ability of deuterated derivatives of 2-amino-2-methylpropionic acid to accumulate in tumors. The possibility of diagnosing a tumor, in particular, a breast tumor 4T1 and glioma C6, is shown on the basis of the observed signal of the deuterated derivative of 2-amino-2-methylpropionic acid.

In the examples below, the MRI scanner Bruker BioSpec BC70/30 USR with the constant field of 7.05 T, equipped with a surface transmitting-and-receiving coil with a diameter of 3 cm and a scan depth of ca. 1 cm was used.

To register deuterium image the FLASH (Fast low angle shot) pulse sequence was used.

For experiments with the broadband excitation the following settings were used: the excitation frequency was determined by $^2$H NMR spectrum and was sfo1≈46.1745 MHz, a rectangular excitation pulse with a width of 1300 Hz and a power of 36 dB, the flip angle FA=30°, the time TR=11.8 MS, echo time TE=4.4 msec, a scan area of 10 cm×10 cm, scan matrix, 50×50, slice thickness 3 cm, bandwidth of 12500 Hz, total scan time 10 minutes (1030 averages).

For experiments with selective excitation the following settings were used: excitation frequency sfo1=46.1745 MHz, a rectangular excitation pulse with a width of 130 Hz and a power of 48 dB, the flip angle FA=30°, the repetition time TR=25 MS, echo time TE=10 MS, a scanning area of 10 cm×10 cm, scan matrix 50×50, slice thickness 3 cm, bandwidth of 25,000 Hz, total scan time 10 minutes.

Example 1. Registration of the Deuterium MR Image and $^2$H NMR Spectrum of the Sample Containing a Dilute Solution of Deuterated 2-Amino-2-Methylpropionic Acid To demonstrate the possibility of registration of the deuterium MR image of a dilute solution of deuterated 2-amino-2-methylpropionic acid, the following experiment was carried out.

A glass vial containing 5 ml of a solution of 2-amino-2-($CD_3$)-3,3,3-$D_3$-propionic acid (5 mg) in distilled water was placed in the cavity of the scanner. The surface transmitting-and-receiving coil with a diameter of 3 cm and a scan depth of about 1 cm was located directly above the vial.

The FIG. 1 shows the $^2$H spectrum of the sample with 2-amino-2-($CD_3$)-3,3,3-$D_3$-propionic acid.

Figure 2:
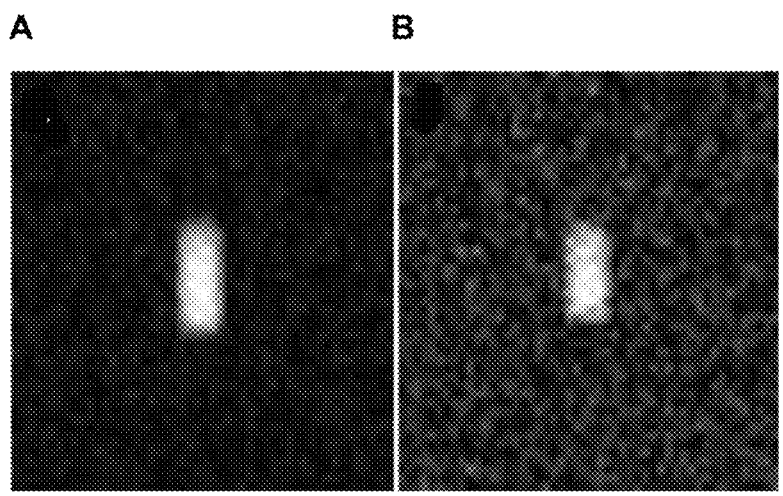

FIG. 2 shows the deuterium MR image of the sample with 2-amino-2-($CD_3$)-3,3,3-$D_3$-propionic acid, obtained using the broadband (left) and selective (right) excitation. Selective excitation can be successfully applied for the registration of deuterium MR image; however, the use of selective excitation is associated with a significant decrease of the ratio signal/noise.

Example 2. The Use of Deuterium MR Imaging to Visualize the 4T1 Breast Carcinoma of the Mouse In Vivo Using 2-amino-2-($CD_3$)-3,3,3-$D_3$-propionic acid as a Diagnostic Agent In this example, experiments were conducted on mice Balb/c inoculated with carcinoma of the breast 4T1 (injection of 5×10$^5$ cells/60 μl under the left front paw for 10 days before experiment) and in healthy Balb/c mice.

An animal no. 1-5 weighing 20 g was injected intraperitoneally with a solution of 20 mg of 2-amino-2-($CD_3$)-3,3,3-$D_3$-propionic acid in 0.5 ml of a saline solution. An animal no. 6-7 weighing 20 g was injected intraperitoneally with a solution of 10 mg (mouse no. 4) or 5 mg (mouse no. 5)

2-amino-2-($CD_3$)-3,3,3-$D_3$-propionic acid in 0.25 ml of a saline solution. After injection, the animal was kept in a separate cage for a specified time (no. 1 with the tumor and no. 2 without the tumor: 40 min; no. 3 with the tumor: 115 min; no. 4 with the tumor: 20 and 360 min; no. 5 and no. 6 with the tumor: 30 min). To register the MR images and spectra an animal was immobilized with isoflurane. The surface transmitting-and-receiving coil was fixed on the body of the mouse on the dorsal side sequentially in two positions (thoracic, kidneys). The FIGS. 3-7 show $^2$H MR images obtained with the use of the broadband excitation of the deuterium nuclei.

Figure 3:
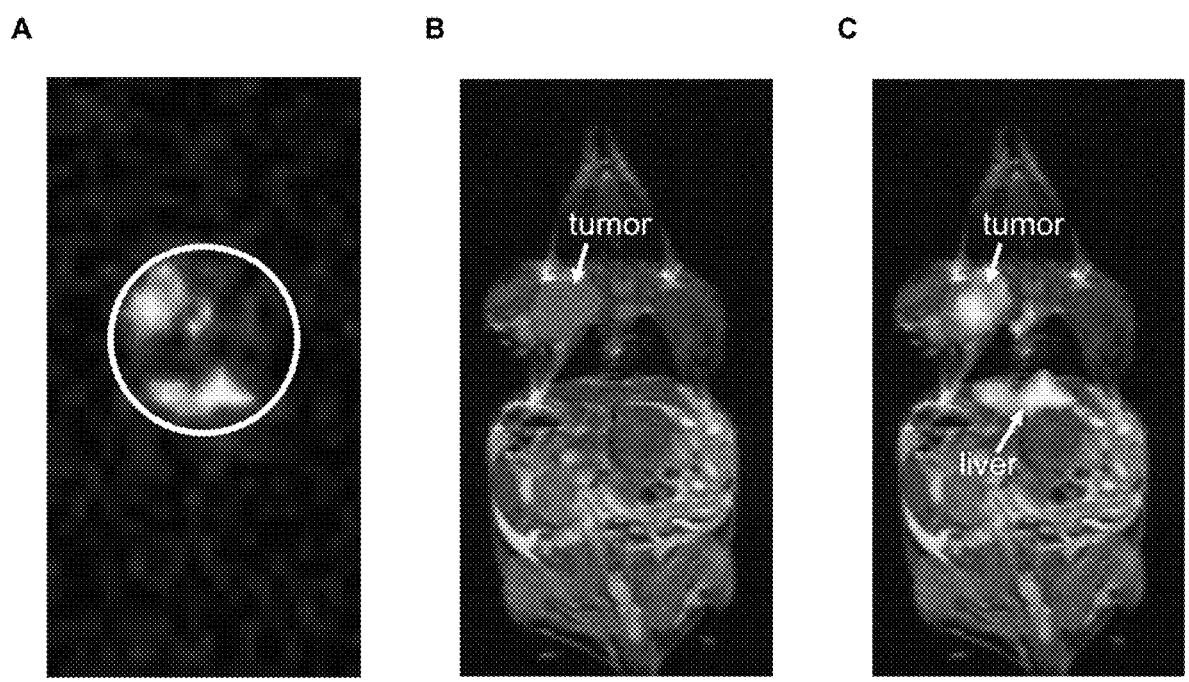
FIG. 3. MR images of the mouse no. 1 with breast carcinoma 4T1 40 min after the administration of 20 mg of 2-amino-2-(CD$_3$)-3,3,3-D$_3$-propionic acid:
  a) $^2$H MRI (the position of the surface coil is shown with a white contour);
  b) $^1$H MRI;
  c) the combined MR image.

FIG. 3 shows the MR image obtained for the mouse no. 1 with the tumor 40 minutes after the administration of 2-amino-2-($CD_3$)-3,3,3-$D_3$-propionic acid: (a) $^2$H MRI (the position of the surface coil is shown in white contour); (b) $^1$H MRI; (c) the superposition $^2$H MRI and $^1$H MRI. This figure demonstrates that the signal of deuterium is localized in the region corresponding to the tumor (signal/noise ratio in the region of the tumor is approximately 6), and also in the area corresponding to the liver, according to $^1$H MRI.

Analysis of the $^2$H MR images obtained for the mouse no. 1 40 min after the administration, showed that the signal/noise ratio in the region of the tumor is approximately 6 (broadband excitation) or about 4 (selective excitation). Thus, the broadband excitation can significantly increase the sensitivity of the method when registering in vivo. It should be noted that when using more sensitive equipment selective excitation may be a more preferable option because it decreases the level of background signal of the heavy water. The signal/noise ratio in the kidneys amounted to approximately 25 (broadband excitation). Thus, we can conclude that the most of the diagnostic agent is accumulated in the kidneys.

Figure 4:
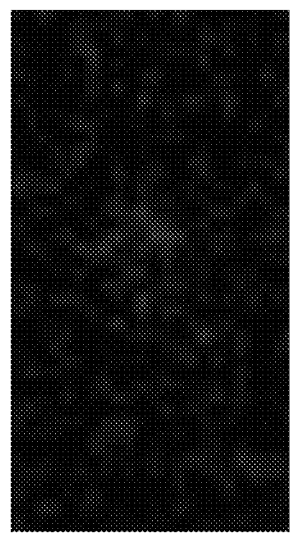
FIG. 4. MR images of the mouse no. 2 without the tumor 40 min after the administration of 20 mg of 2-amino-2-(CD$_3$)-3,3,3-D$_3$-propionic acid:
  a) $^2$H MRI;
  b) $^1$H MRI.
Figure 4:

FIG. 4 shows the MR image obtained for a control mouse no. 2 without the tumor 40 minutes after the administration of 2-amino-2-($CD_3$)-3,3,3-$D_3$-propionic acid: (a) $^2$H MRI; (b) $^1$H MRI; (C) the superposition $^2$H MRI and $^1$H MRI. In this figure, the signal of deuterium, in contrast to FIG. 3, is localized in the region corresponding to the liver according to $^1$H MRI.

Based on the results illustrated by FIGS. 3 and 4, we can conclude that:
1) 2-amino-2-($CD_3$)-3,3,3-$D_3$-propionic acid accumulates in tumor tissue in vivo up to the concentration that is sufficient for visualization using $^2$H MRI;
2) 2-amino-2-($CD_3$)-3,3,3-$D_3$-propionic acid can be used as the diagnostic agent for the detection of malignant tumors using $^2$H MRI.

Figure 5:
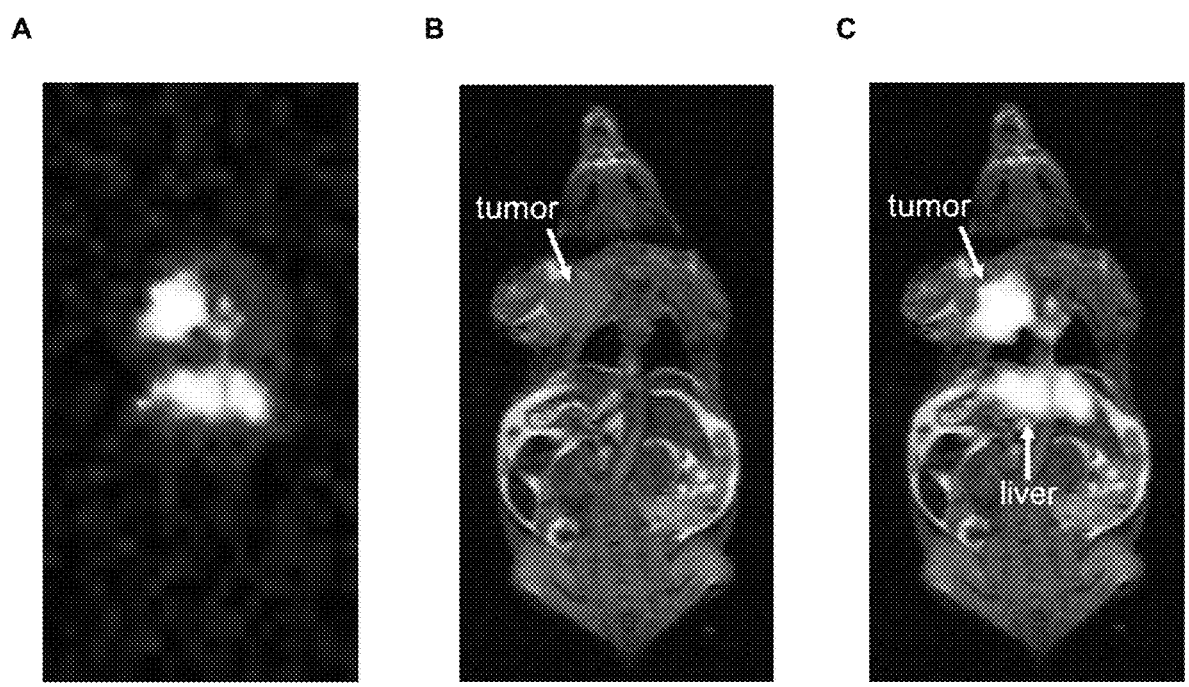
FIG. 5. MR images of the mouse no. 3 with breast carcinoma 4T1 115 minutes after the administration of 20 mg of 2-amino-2-(CD$_3$)-3,3,3-D$_3$-propionic acid:
  a) $^2$H MRI;
  b) $^1$H MRI;
  c) the combined MR image.

FIG. 5 shows the MR image obtained for the mouse no. 3 with the tumor 115 minutes after the administration of 2-amino-2-($CD_3$)-3,3,3-$D_3$-propionic acid: (a) $^2$H MRI; (b) $^1$H MRI; (C) the superposition $^2$H MRI and $^1$H MRI. This figure demonstrates that the signal of deuterium is localized in the region corresponding to the tumor and in the area corresponding to the liver, according to $^1$H MRI.

Figure 6:
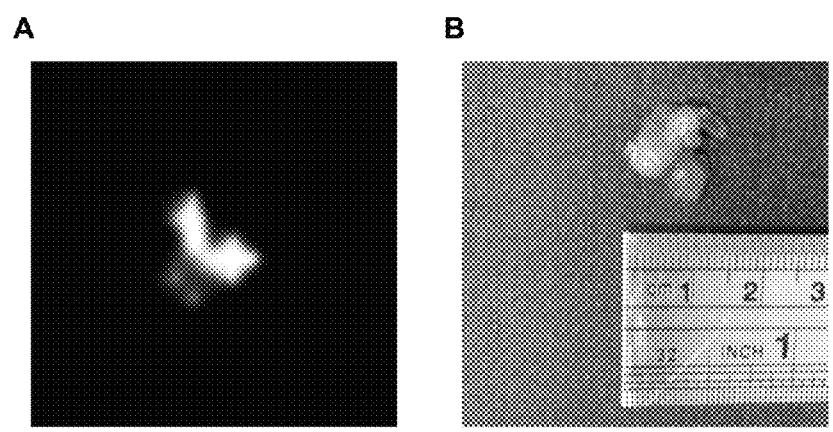
FIG. 6. $^2$H MR image (a) and photograph (b) of tumors recovered from the mouse no. 3 in 150 minutes after injection of 20 mg of 2-amino-2-(CD$_3$)-3,3,3-D$_3$-propionic acid.

The FIG. 6 shows: deuterium MR image (a) and photograph (b) of tumors excised from the mouse no. 3 150 minutes after injection of 2-amino-2-($CD_3$)-3,3,3-$D_3$-propionic acid. This figure shows that isolated tumor is clearly visible on deuterium MR image, due to sufficient accumulation of 2-amino-2-($CD_3$)-3,3,3-$D_3$-propionic acid.

Figure 7:
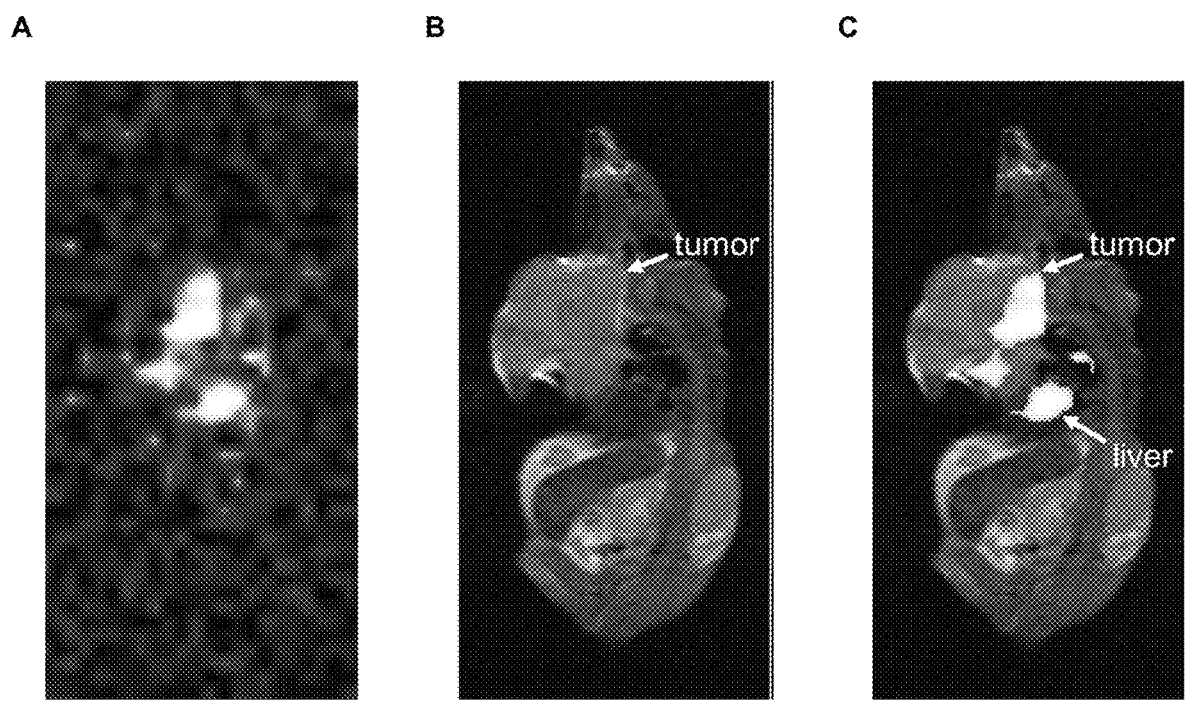
FIG. 7. MR images of the mouse no. 4 with breast carcinoma 4T1 20 min after injection of 20 mg of 2-amino-2-(CD$_3$)-3,3,3-D$_3$-propionic acid:
  a) $^2$H MRI;
  b) $^1$H MRI;
  c) the combined MR image.

FIG. 7 shows the MR image obtained for the mouse no. 4 with the tumor 20 min after the administration of 2-amino-2-($CD_3$)-3,3,3-$D_3$-propionic acid: (a) $^2$H MRI; (b) $^1$H MRI; (C) the superposition $^2$H MRI and $^1$H MRI. This figure demonstrates that the signal of deuterium is localized in the region corresponding to the most recently developed and actively growing parts of the tumor, and also in the area corresponding to the liver, according to $^1$H MRI.

Figure 8:
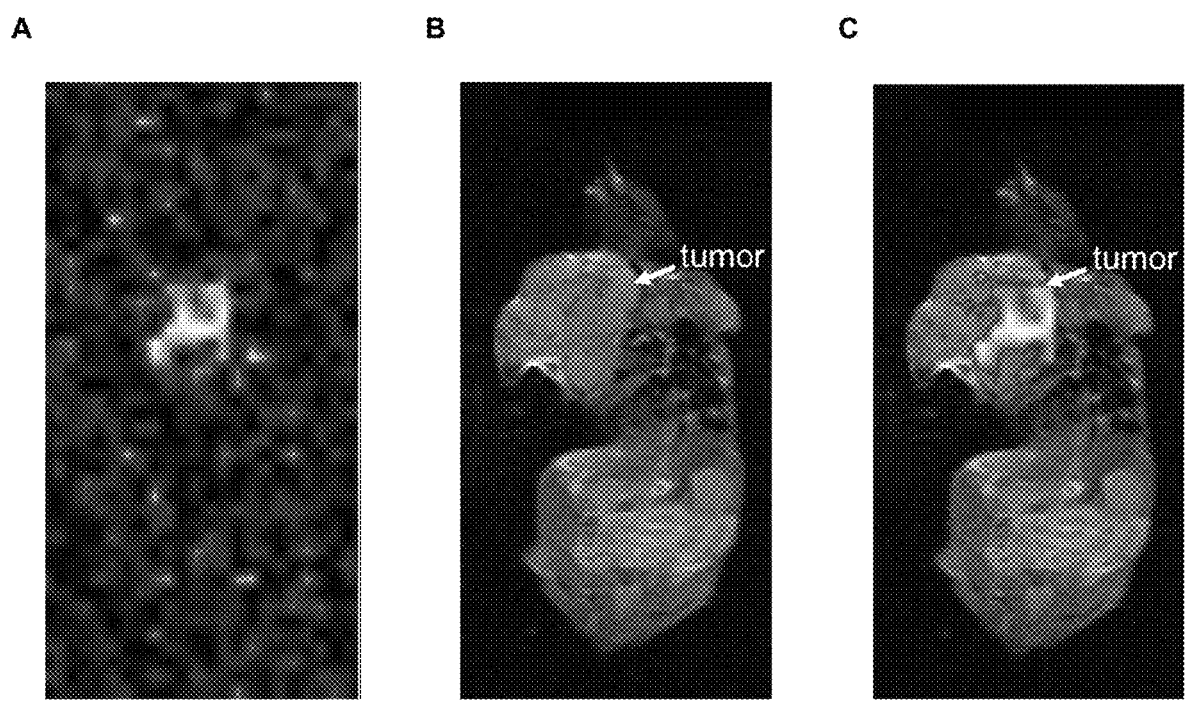
FIG. 8. MR images of the mouse no. 4 with breast carcinoma 4T1 360 min after the administration of 20 of mg 2-amino-2-(CD$_3$)-3,3,3-D$_3$-propionic acid:
  a) $^2$H MRI;
  b) $^1$H MRI;
  c) the combined MR image.

FIG. 8 shows the MR image obtained for the mouse no. 4 with the tumor 360 minutes after the administration of 2-amino-2-($CD_3$)-3,3,3-$D_3$-propionic acid: (a) $^2$H MRI; (b) $^1$H MRI; (C) the superposition $^2$H MRI and $^1$H MRI. This figure demonstrates that the signal of deuterium is localized in the region corresponding to the most recently developed and actively growing parts of the tumor according to $^1$H MRI.

Based on the results illustrated by FIGS. 7 and 8 we can conclude that in case of extensive tumors the diagnostic agent according to the invention allows to visualize the most actively growing parts of the tumor. In addition, on the basis of these results we conclude that the diagnostic agent is removed from the tumor within several hours.

Figure 9:
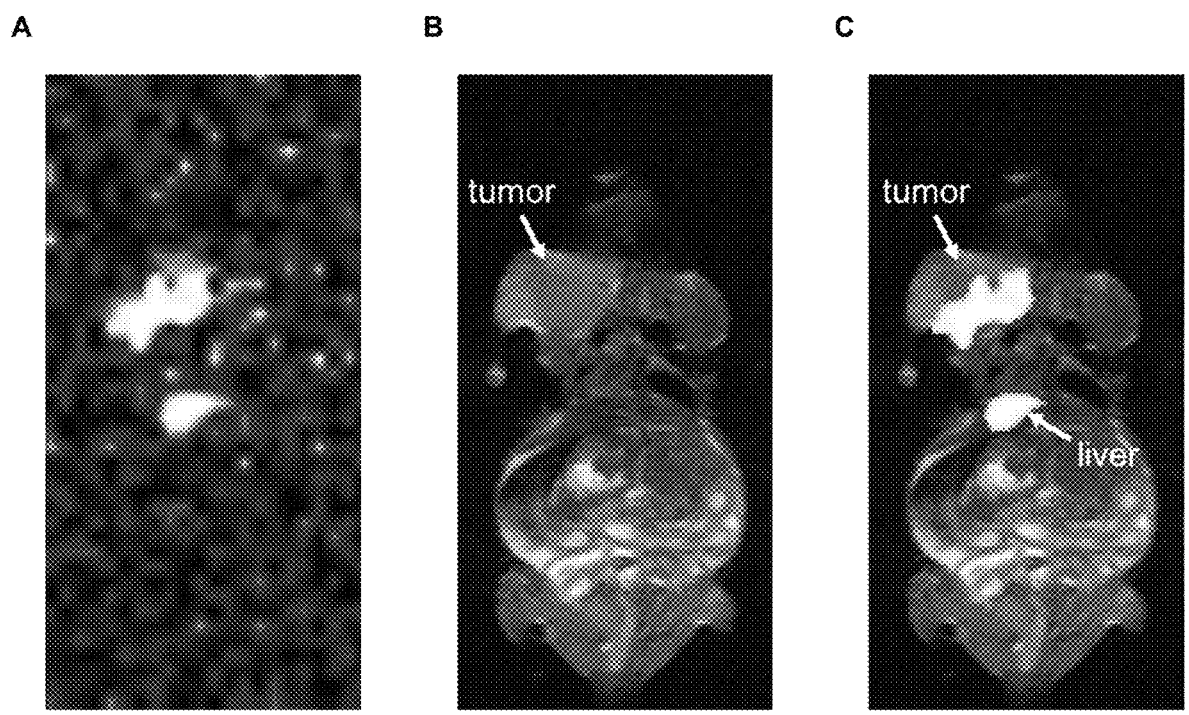
FIG. 9. MR images of mouse no. 5 with breast carcinoma 4T1 30 min after the administration of 10 mg of 2-amino-2-(CD$_3$)-3,3,3-D$_3$-propionic acid:
  a) $^2$H MRI;
  b) $^1$H MRI;
  c) the combined MR image.

FIG. 9 shows the MR image obtained for the mouse no. 5 with the tumor 30 minutes after the administration of 10 mg 2-amino-2-($CD_3$)-3,3,3-$D_3$-propionic acid: (a) $^2$H MRI; (b) $^1$H MRI; (C) the superposition $^2$H MRI and $^1$H MRI. This figure demonstrates that the signal of deuterium is localized in the region corresponding to individual parts of the tumor, probably corresponding to zones of the most intense growth, as well as in the area corresponding to the liver, according to $^1$H MRI.

Figure 10:
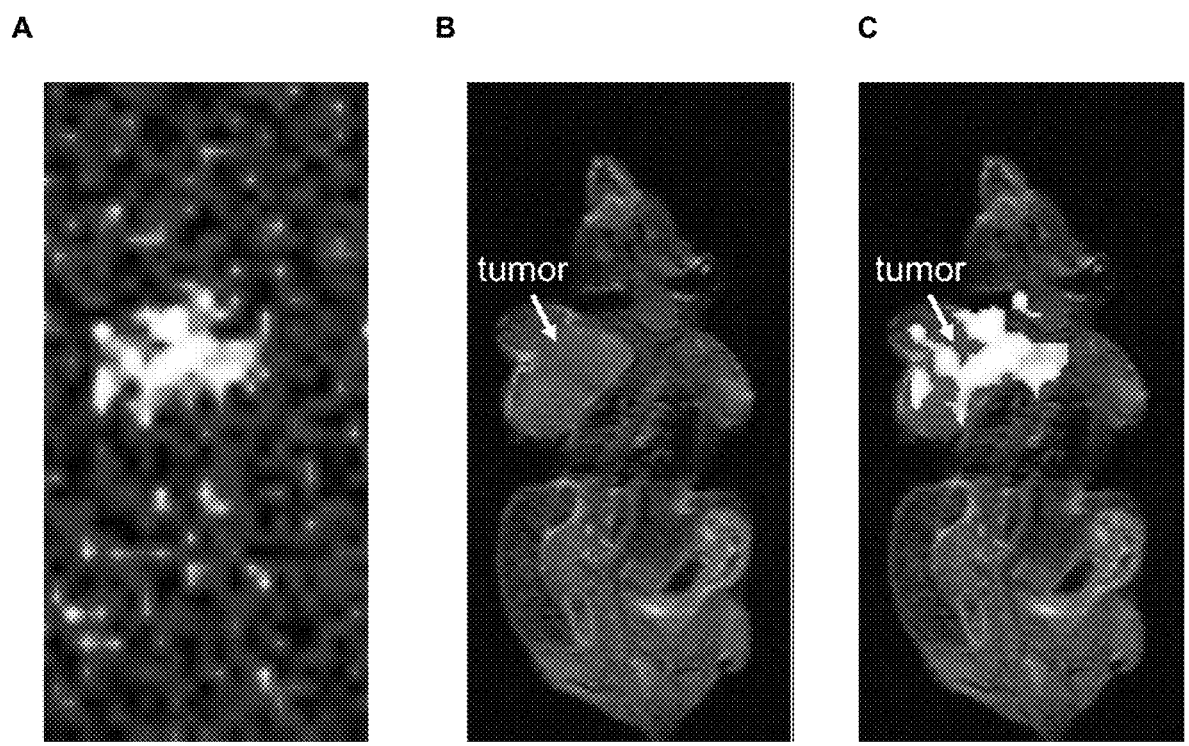
FIG. 10. MR images of the mouse no. 6 with breast carcinoma 4T1 30 min after the administration of 5 mg of 2-amino-2-(CD$_3$)-3,3,3-D$_3$-propionic acid:
  a) $^2$H MRI;
  b) $^1$H MRI;
  c) the combined MR image.

FIG. 10 shows the MR image obtained for the mouse no. 6 with the tumor 30 minutes after the administration of 5 mg of 2-amino-2-($CD_3$)-3,3,3-$D_3$-propionic acid: (a) $^2$H MRI; (b) $^1$H MRI; (C) the superposition $^2$H MRI and $^1$H MRI. This figure demonstrates that the signal of deuterium is localized in the region corresponding to individual parts of the tumor, probably corresponding to zones of the most intense growth, as well as in the area corresponding to the liver, according to $^1$H MRI.

It should be noted that for other animals and for humans, and in case of another route of administration (e.g. oral or intravenous) and/or other malignant diseases the range of administered diagnostic agent may be different. In particular, considering the allometric equations describing the pharmacokinetics of agents in organisms of different size, we can expect the reduction of a dose needed for human several-fold in comparison with the described doses.

Based on the results illustrated by FIGS. 3, 5, 7 and 8 we can conclude that the allowable time range between the administration of 2-amino-2-($CD_3$)-3,3,3-$D_3$-propionic acid and detection of deuterium can be, in particular, 20-360 min. It should be noted that for other animals and for humans this range can be significantly wider due to the difference in pharmacokinetics.

Example 3. The Use of Deuterium Tomography for the Visualization of Glioma C6 in Rats In Vivo Using 2-amino-2-($CD_3$)-3,3,3-$D_3$-propionic acid as the Diagnostic Agent In this example, experiments were conducted on Wistar rats inoculated with C6 glioma and in healthy Wistar rats.

An animal with the weight of 210 g was injected intraperitoneally a solution of 150 mg of 2-amino-2-($CD_3$)-3,3,3-$D_3$-propionic acid in 1.5 ml of a saline solution. After injection, the animal was kept in a separate cage with free access to food and water. To register the MR images and spectra an animal was immobilized with isoflurane. The surface transmitting-and-receiving coil was fixed over the head of the rat.

Figure 11:
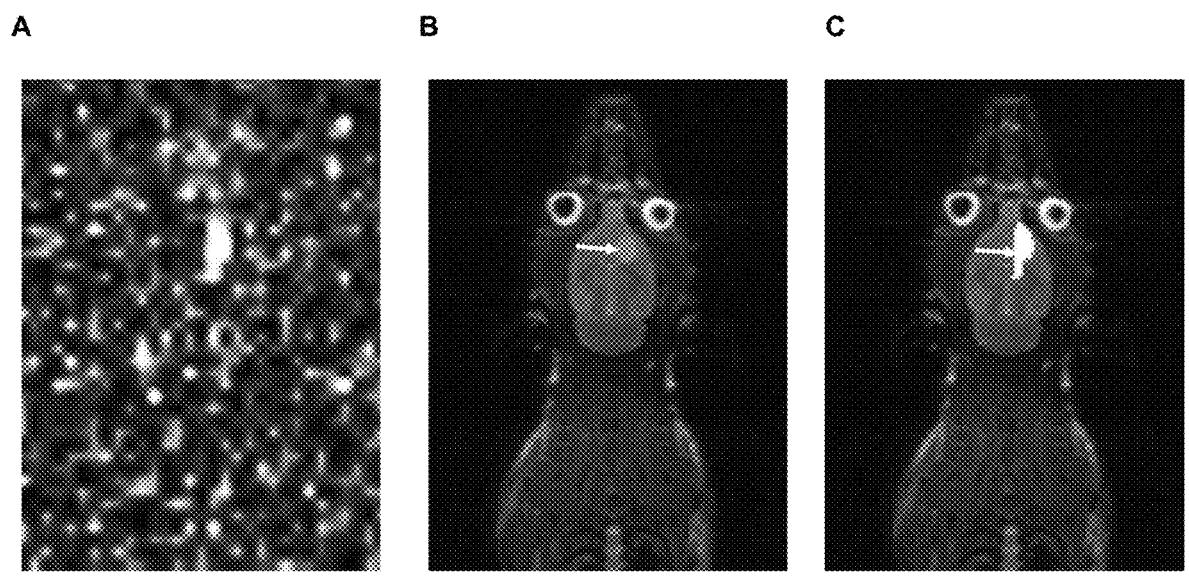
FIG. 11. MR images of a rat with C6 glioma 3 hours after the administration of 150 mg of 2-amino-2-(CD$_3$)-3,3,3-D$_3$-propionic acid:
  a) $^2$H MRI;
  b) $^1$H MRI;
  c) the combined MR image.

FIG. 11 shows the MR image obtained for the rat with a tumor 4 hours after the administration of 2-amino-2-($CD_3$)-3,3,3-$D_3$-propionic acid: (a) untreated $^2H$ MRI; (b) $^1H$ MRI; (c) superposition of $^2H$ MRI and $^1H$ MRI. This figure demonstrates that the signal of deuterium is localized in the region corresponding to the tumor according to $^1H$ MRI.

Figure 12:
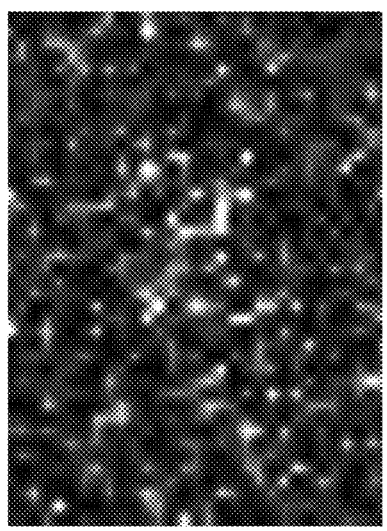
FIG. 12. MR images of a control rat without tumor in 3 hours after the administration of 150 mg of 2-amino-2-(CD$_3$)-3,3,3-D$_3$-propionic acid:
  a) $^2$H MRI;
  b) $^1$H MRI.
Figure 12:
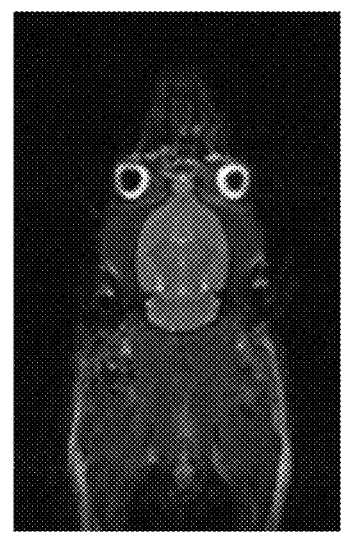

FIG. 12 shows the MR image obtained for the rats without tumors 4 hours after the administration of 2-amino-2-($CD_3$)-3,3,3-$D_3$-propionic acid: (a) untreated $^2H$ MRI; (b) $^1H$ MRI. This figure demonstrates that the signal of deuterium does not show a clear localization.

Based on the results illustrated by the FIGS. 11 and 12, it can be concluded that the diagnostic agent according to the invention, in particular comprising 2-amino-2-($CD_3$)-3,3,3-$D_3$-propionic acid can be used as a diagnostic agent for the detection of malignant tumors, including glioma, using $^2H$ MRI.

Despite the fact that the invention has been described with reference to the disclosed embodiments, for specialists in this field it should be obvious that the specific details of the described experiments are given only for the purpose of illustrating the present invention and they should not be construed as in any way limiting the scope of the invention. It should be understood that it is possible to implement various modifications without deviation from the essence of the present invention.

The invention claimed is:

1. A diagnostic agent, comprising a deuterated derivative of 2-amino-2-methylpropionic acid and/or 2-(N-methylamino)-2-methylpropionic acid and/or its pharmaceutically acceptable salt, or a mixture of at least two different deuterated derivatives of 2-amino-2-methylpropionic acid and/or 2-(N-methylamino)-2-methylpropionic acid and/or its pharmaceutically acceptable salts, formulated for in vivo diagnosis of an oncological disease in a human subject by magnetic resonance imaging and/or magnetic resonance spectroscopy at a frequency of deuterium nuclei,
wherein the diagnostic agent is formulated to fail to accumulate to indicate the absence of cancer in the subject where the deuterated derivative of 2-amino-2-methylpropionic acid is 2-amino-2-($CD_3$)-3,3,3-$D_3$-propionic acid or 2-amino -2-($CD_2H$)-3,3,3-$D_3$-propionic acid or 2-amino-2-($CDH_2$)-3,3,3-$D_3$-propionic acid or 2-amino -2-methyl-3,3,3-$D_3$- propionic acid or 2-amino-2-($CD_2H$)-3,3-$D_2$-propionic acid or 2-amino-2-($CDH_2$)-3,3-$D_2$-propionic acid or 2-amino-2-methyl-3,3-$D_2$-propionic acid or 2-amino-2-($CDH_2$)-3-D-propionic acid or 2-amino-2-methyl-3-D-propionic acid and wherein the deuterated derivative of 2-(N-methylamino)-2-methylpropionic acid is a 2-methylamino-2-($CD_3$)-3,3,3-$D_3$-propionic acid or 2-(N-($CD_3$)amino)-2-methylpropionic acid or 2-(N-($CD_3$)amino)-2-($CD_3$)-3,3,3-$D_3$-propionic acid.

2. The diagnostic agent according to claim 1, further comprising at least one pharmaceutically acceptable excipient.

3. The diagnostic agent according to claim 1, further comprising non-deuterated 2-amino-2-methylpropionic acid or 2-(N-methylamino)-2-methylpropionic acid.

4. The diagnostic agent according to claim 1, wherein the deuterated derivative of 2-amino-2-methylpropionic acid or 2-(N-methylamino)-2-methylpropionic acid and/or its pharmaceutically acceptable salt along with deuterium atoms bound to carbon atoms contains deuterium atoms that partially or completely replace mobile hydrogen atoms attached to oxygen and/or nitrogen atoms.

5. A method for diagnosing an oncological disease in a subject, the method comprising:
a) administering to the subject the diagnostic agent according to claim 1;
b) conducting magnetic resonance imaging and/or magnetic resonance spectroscopy at the frequency of deuterium nuclei after administration of the diagnostic agent after a period of time sufficient for accumulation of said diagnostic agent in tumor tissue, for obtaining, respectively, a MR image and/or an NMR spectrum; and
c) diagnosing presence or absence of the oncological disease based on an observed signal intensity of deuterium nuclei, reflecting the level of accumulation of diagnostic agent,
wherein the diagnostic agent is formulated to fail to accumulate to indicate the absence of cancer in the subject.

6. The method according to claim 5, wherein at least one additional medical study, selected from magnetic resonance imaging at the frequency of nuclei differing from deuterium, or ultrasound, or computed tomography, or X-ray, or palpation, or biopsy, or screening of biological materials for tumor markers, or radionuclide diagnosis or physical examination is carried out.

7. The method according to claim 5, wherein diagnosing presence or absence of the oncological disease is based on a comparison of the observed signal intensity of deuterium nuclei in the examined subject with a typical intensity of the signal observed in healthy subjects in the corresponding tissue or organ.

8. The method according to claim 6, wherein diagnosing presence or absence of the oncological disease is based on a comparison of the observed signal intensity of deuterium nuclei in regions corresponding to normal and pathological tissues according to the at least one additional medical study.

9. The method according to claim 6, wherein diagnosing presence or absence of the oncological disease is based on a comparison of the observed signal intensity of deuterium nuclei in neighboring voxels that are located at different sides of an interface between normal tissue and tissue suspicious for a tumor according to $^1H$ MRI.

10. The method according to claim 6, wherein diagnosing presence or absence of the oncological disease is based on comparison of deuterium images with $^1H$ magnetic resonance images from the same subject.

11. The method according to claim 5, wherein the observed signal intensity of deuterium nuclei and/or its change in time allows for a conclusion to be made on structure, malignancy grade, aggressiveness, or degree of differentiation of a tumor.

12. The method according to claim 5, wherein the oncological disease is breast cancer or glioma.

13. The method according to claim 5, wherein during MR image registration a selective excitation of deuterium nuclei contained in the deuterated derivative of 2-amino-2-methylpropionic acid or 2-(N-methylamino)-2-methylpropionic acid and/or of its pharmaceutically acceptable salts, or of a mixture of deuterated derivatives of 2-amino-2-methylpropionic acid and/or 2-(N-methylamino)-2-methylpropionic acid and/or its pharmaceutically acceptable salts is used.

14. The diagnostic agent according to claim 1, wherein the diagnostic agent is formulated to provide a diagnostic indication in connection with magnetic resonance tomography and/or magnetic resonance spectroscopy carried out in 20-360 minutes after administration of the diagnostic agent.

15. The diagnostic agent according to claim 1, wherein the diagnostic agent is formulated to provide a diagnostic indication when administered to the subject in an amount corresponding to 0.25-1 g of deuterated derivative of 2-amino-2-methylpropionic acid or 2-(N-methylamino)-2-methylpropionic acid and/or its pharmaceutically acceptable salts, or mixtures deuterated derivatives of 2-amino-2-methylpropionic acid and/or 2-(N-methylamino)-2-methylpropionic acid and/or its pharmaceutically acceptable salt per 1 kg of body weight of the subject.

16. The diagnostic agent according to claim 1, wherein the term deuterated or deuterated derivative refers to a compound containing deuterium associated with carbon in excess of its natural content, at least in one position, and
  wherein the term mixture of at least two different deuterated derivatives refers to a mixture of compounds containing deuterium in different positions of the molecule, or containing different amounts of deuterium in the same position.

17. The diagnostic agent according to claim 1, wherein the diagnostic agent is formulated so that deuterium nuclei therein are registerable in vivo via selective excitation thereof during MR imaging when cancer is present in the patient.

* * * * *